United States Patent
Hudkins

(10) Patent No.: US 9,441,236 B2
(45) Date of Patent: *Sep. 13, 2016

(54) TRANSGENIC BIOLUMINESCENT PLANTS

(71) Applicant: Bruce Eric Hudkins, Tulsa, OK (US)

(72) Inventor: Bruce Eric Hudkins, Tulsa, OK (US)

(*) Notice: Subject to any disclaimer, the term of this patent is extended or adjusted under 35 U.S.C. 154(b) by 142 days.

This patent is subject to a terminal disclaimer.

(21) Appl. No.: 14/496,758

(22) Filed: Sep. 25, 2014

(65) Prior Publication Data

US 2015/0026844 A1 Jan. 22, 2015

Related U.S. Application Data

(60) Continuation of application No. 13/109,623, filed on Jun. 2, 2011, now Pat. No. 8,853,491, which is a continuation of application No. 12/704,330, filed on Feb. 11, 2010, now Pat. No. 7,994,396, which is a division of application No. 11/419,108, filed on May 18, 2006, now Pat. No. 7,663,022, which is a continuation-in-part of application No. 10/195,283, filed on Jul. 15, 2002, now Pat. No. 7,049,483.

(51) Int. Cl.
*C12N 15/82* (2006.01)

(52) U.S. Cl.
CPC ......... *C12N 15/8261* (2013.01); *C12N 15/825* (2013.01); *C12N 15/8205* (2013.01); *C12N 15/8212* (2013.01); *C12N 15/8225* (2013.01); *C12N 15/8237* (2013.01); *C12N 15/8239* (2013.01); *C12N 15/8242* (2013.01)

(58) Field of Classification Search
None
See application file for complete search history.

(56) References Cited

U.S. PATENT DOCUMENTS 5,741,668 A * 4/1998 Ward .................. C07D 277/68
435/189

OTHER PUBLICATIONS

Mayerhofer et al. The Plant Journal 7(6): 1031-1038 (1995).*
Lorenz et al. Proc. Natl. Acad. Sci. USA 88: 4438-4442 (1991).*
Stewart, C.N. Plant Cell Reports 20: 376-382 (published online Jun. 7, 2001).*
Matz et al. Nature Biotechnology 17(10): 969-973 (1999).*
Tsien, R.Y. Nature Biotechnology 17(10): 956-957 (1999).*

* cited by examiner

*Primary Examiner* — David T Fox
(74) *Attorney, Agent, or Firm* — Head, Johnson & Kachigian, P.C.

(57) ABSTRACT

Transgenic plants, and a method for making the same, wherein genes encoding the enzyme luciferase and its corresponding substrate luciferin are incorporated into a native plant genome. Once transformed into plant cells, these genes may be regulated such that under certain endogenous or exogenous conditions, their expression in the mature plant results in bioluminescence. Different luciferin/luciferase complexes and/or mechanisms of regulation may be utilized for these transgenic plants, depending on a variety of factors such as plant species and the circumstances under which a biolmuniescent reaction is desired. Phototransformation may be utilized to vary the wavelength of light emitted from the mature plant.

22 Claims, 2 Drawing Sheets

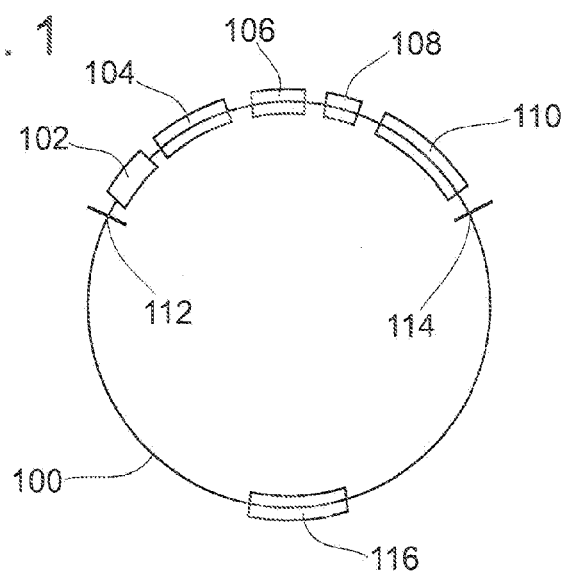
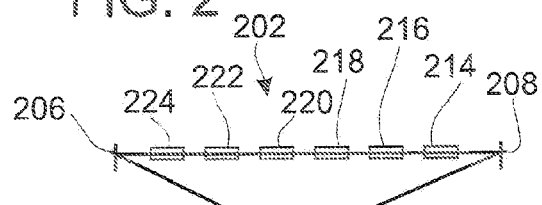
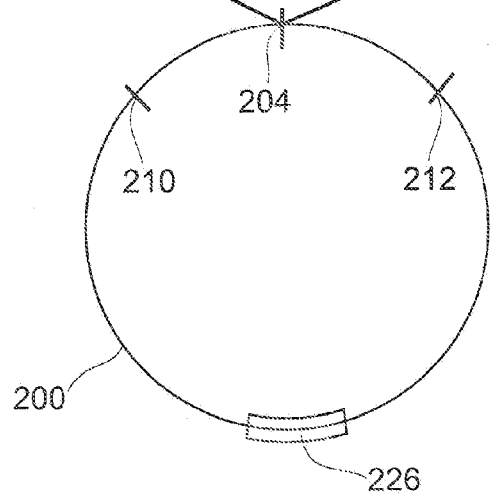
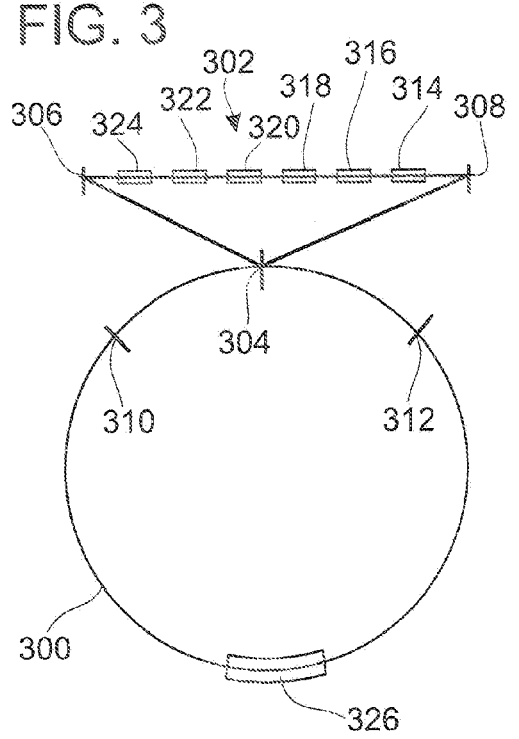

TRANSGENIC BIOLUMINESCENT PLANTS

CROSS-REFERENCE TO RELATED APPLICATIONS

This application claims priority to and is a continuation application of U.S. patent application Ser. No. 13/109,623 filed Jun. 2, 2011, now U.S. Pat. No. 8,853,491, which is a continuation of U.S. patent application Ser. No. 12/704,330, filed Feb. 11, 2010, now U.S. Pat. No. 7,994,396, which is a divisional application of U.S. patent application Ser. No. 11/419,108 filed May 18, 2006, now U.S. Pat. No. 7,663,022, which is a continuation-in-part patent application of U.S. patent application Ser. No. 10/195,283 filed Jul. 15, 2002, now U.S. Pat. No. 7,049,483, each of which is incorporated herein by reference in their entirety.

REFERENCE TO A SEQUENCE LISTING COMPACT DISC APPENDIX

See Sequence Listing, attached hereto.

BACKGROUND OF THE INVENTION

1. Field of the Invention

This invention relates generally to transgenic bioluminescent plants, and more particularly to plants, cells of which have been transfected via *Agrobacterium*, with nucleic acid molecules encoding luciferase and luciferin such that the resulting plant luminesces, in whole or in part. The transfected nucleic acid molecules may be operably linked to, and their expression regulated by, promoters in order to control the incidence, timing and duration of the genetically engineered bioluminescence. Bioluminescent emissions may further be transformed such that light of varying wavelengths is emitted from the plants.

2. Description of the Related Art

A certain class of enzymes, known as luciferases, bioluminesce in the presence of compatible substrates, referred to generally as luciferins. Luciferases are a broad class of proteins that exhibit little homology and are found in terrestrial and marine bacteria, jellyfish, fireflies and a variety of other organisms. Nucleic acid molecules which encode luciferase have been identified, and their bioluminescent activities have been used extensively to study gene regulation and expression. By inserting luciferase protein encoding sequences downstream from a promoter to be studied, one may tell when that promoter has been activated by the resulting bioluminescence.

Luciferins, the substrates for luciferases, tend to be complex organic molecules. Bacterial luciferins, such as those found in *Vibrio, Photobacterium* and *Xenorhabdus*, have been described as a complex of fatty acid reductase proteins. Some luciferins are thought to be formed by means of complex catabolic pathways. Others, such as the jellyfish luciferin coelenterazine, result from the cyclization of amino acids of a polypeptide. Until recently, nucleic acid molecules encoding the luciferin complex were not known. This meant that in order to detect luciferase, luciferin had to be applied directly to organisms expressing luciferase. The luciferin had to be absorbed by the target, and as a result, suitable hosts were generally limited to cells, relatively thin tissue cultures, and very small seedlings. Organisms or cells expressing luciferase were lysed and exposed to a luciferin solution, which killed the host organism.

There has been a significant amount of work done to improve the use of luciferase in studying gene expression; however, all efforts have been limited by the inability to produce in vivo bioluminescence without the addition of chemicals, outside of a laboratory environment, and in larger organisms.

It is therefore desirable to provide a method for causing bioluminescence in a mature multicellular organism, such as a plant.

It is also desirable to provide a method for inducing bioluminescence without the need to apply chemicals to an organism.

It is also desirable to provide for a mature plant capable of bioluminescence outside of a laboratory setting and without the need of applying special chemicals.

It is also desirable to provide a mature plant capable of bioluminescence where the timing of that bioluminescence is controlled, or when such bioluminescence can communicate important information about the relative health or condition of the plant.

It is also desirable to provide a mature plant capable of bioluminescence where the bioluminescent emission can be transformed and the wavelength of the light emitted from the plant can vary.

SUMMARY OF THE INVENTION

In general, the invention relates to a transgenic autoluminescent plant and/or plant cell and/or plant seed having within its genome a lux gene encoding a luciferase, a lux gene encoding a luciferin that is compatible with said luciferase, and at least one means for regulation of autoluminescent expression of said lux genes. The plant may also include within the genome of the plant cell at least one gene encoding a phototransformative protein and at least one means for regulation of expression of the gene encoding the phototransformative protein. The phototransformative protein may be a green fluorescent protein or a genetic mutant of green fluorescent protein. Further, the phototransformative protein may be a green fluorescent protein, a blue fluorescent protein, a cyan fluorescent protein, a yellow fluorescent protein, an orange fluorescent protein or a red fluorescent protein. In addition, the means for regulating expression of the gene encoding the phototransformative protein may be a 5' promoter.

The means for regulation of expression of the lux genes may include at least one stress-linked promoter that regulates expression under a set of conditions related to the health of said mature plant, such as hydration, disease, infestation, temperature, ripeness, and adequacy of nutrients. For example, the stress-linked promoter can include a fungal-inducible promoter, a wound-inducible promoter, a general stress-inducible promoter, a phosphate-inducible promoter or a nitrogen-inducible promoter. Additionally, the plant cell may contain at least one light-inducible promoter is the RuBisCO 5' promoter or the CAB2 promoter.

BRIEF DESCRIPTION OF THE DRAWINGS

FIGS. 1, 2 and 3 are diagrammatic views of each of the three recombinant DNA plasmids constructed in accordance with an illustrative embodiment of the transgenic bioluminescent plants disclosed herein.

DETAILED DESCRIPTION OF THE INVENTION

Figure 4:
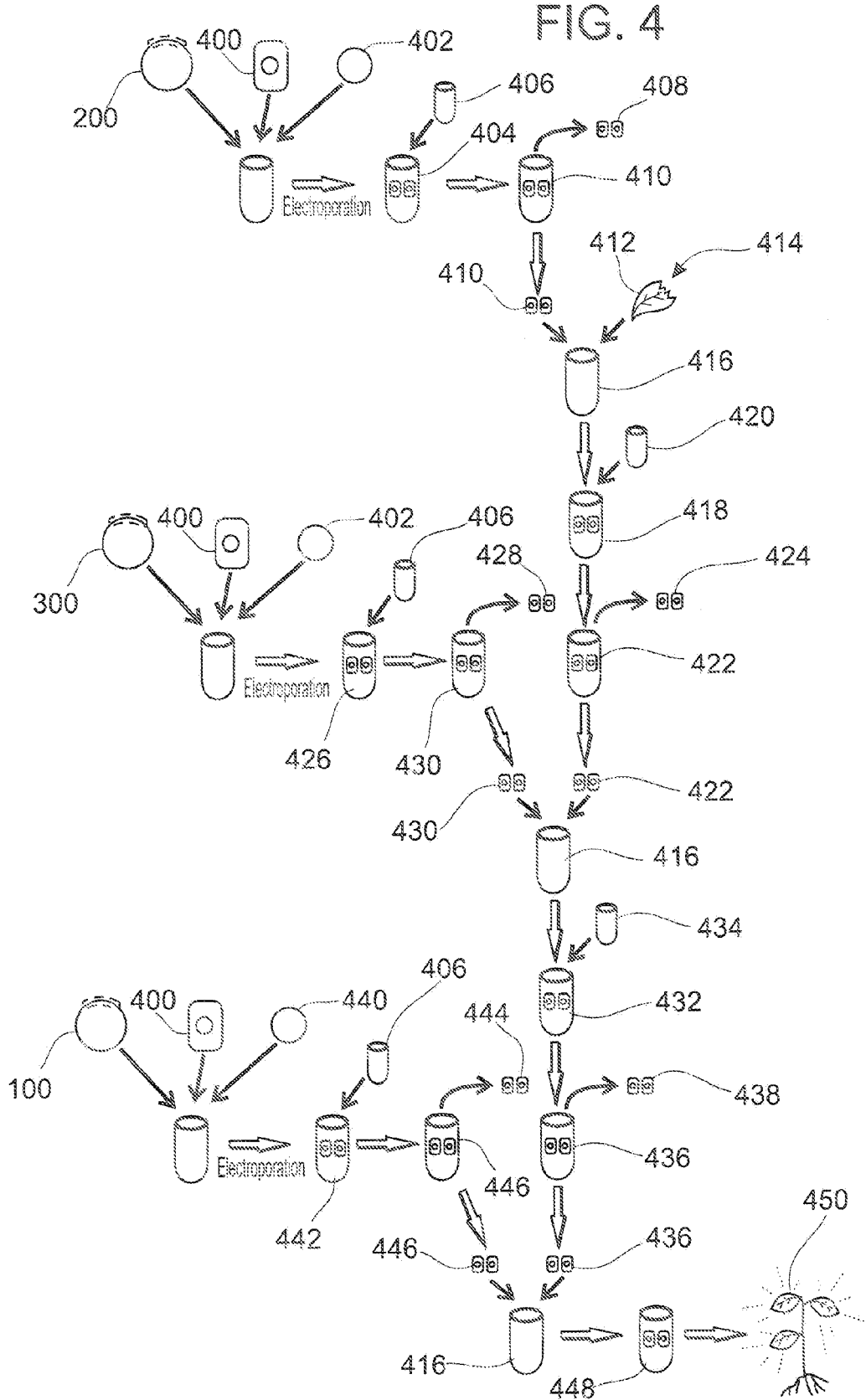
FIG. 4 is a diagrammatic view of an example of a method for transfecting recombinant DNA sequences into *Agrobacterium* and subsequently into intermediate plant cell cultures or calli and ultimately into a callus that will become the mature plant in accordance with an illustrative embodiment of the transgenic bioluminescent plants disclosed herein.

The plants and methods discussed herein are merely illustrative of specific manners in which to make and use the invention and are not to be interpreted as limiting the scope of the instant invention.

While the plants and methods have been described with a certain degree of particularity, it is to be noted that many modifications may be made in the construction and the arrangement of the structural and functional details without departing from the spirit and scope of this disclosure. It is understood that the plants and methods are not limited to the embodiments set forth herein for purposes of exemplification.

It is possible that in some or all plants, bioluminescence will be enhanced by directing the luciferase and corresponding luciferin to a specific location within the plant. This may be accomplished using control sequences that result in the addition of amino acids at either the N- or C-termini of the proteins. These added amino acids utilize mechanisms within a plant to direct the protein to which they are attached to specific regions of the plant cell. For example, some control sequences direct proteins to the chloroplasts, while others result in the protein being attached to a membrane. Control sequences may also be used to regulate both the translation and transcription of a polynucleotide sequence. These control sequences may be employed to regulate the concentration of the protein within the organism that is expressing it.

Some control sequences require the inclusion of a second, regulatory sequence. For example, some control sequences inhibit gene translation only when an inhibitor protein is present. In this situation, it is necessary to add to the vector a sequence that encodes the inhibitor protein. This inhibitor protein sequence may in turn have its own control sequences up- or downstream from it. It is even possible for an inhibitor protein sequence to have a control sequence that itself requires a second inhibitor protein sequence in order to function properly. In addition, just as there are control sequences that require inhibitor proteins, there are also control sequences that require activation proteins that increase gene translation. These control sequences require the addition of an activation protein sequence. There are also control sequences that regulate expression of coding sequences at the transcription stage. These sequences inhibit or facilitate ribosomal activity on mRNA. The selection of particular control sequences, promoters and vectors to be used for a particular plant will be depend on the method of transformation, the plant into which the vector is being introduced, and personal discretion.

The invention disclosed herein relates to the use of two or more nucleotide sequences to construct a bioluminescence mechanism within plant cells. Under conditions suitable for expression, such as darkness, drought or infestation, the resulting mature plants will luminesce for a given time period. Depending upon the aim of the invention, it may be preferable to have the plant luminesce throughout the evening or for at least a few hours following dusk.

The invention may be applied to any type of plant, and is especially desirable in food crops, landscaping and houseplants. Trees, shrubs, flowers and grass are desirable plants for use in the present invention. These are plants typically found in the landscaping of a home's curtilage, where increased security and pleasant appearance are highly desirable. Both monocotyledons such as grasses and palms, and dicotyledons such as trees and most flowers, may be used in the present invention. Current plant transformation techniques, discussed below, now provide a means for genetically modifying any type of plant.

Bacterial luciferases have been identified in a number of species of bacteria. Among them are the genera *Vibrio*, *Photobacterium*, and *Xenorhabdus*. Once a suitable luciferase/luciferin bioluminescence mechanism has been chosen, such as the lux operon from *Vibrio fischeri* described in detail below, appropriate nucleotide sequences are assembled into one or more vectors or plasmids which are in turn utilized to transform or 'transfect' plant cells. For example, a bacterial plasmid derived from *Agrobacterium tumefaciens* or *Agrobacterium rhizogenes* may be utilized in transfecting the plant cell. The *Agrobacterium* plasmid contains a T-DNA segment that it transfers into the chromosome of a plant cell it has infected. The T-DNA of the wild type bacterium may be replaced with a polynucleotide up to 25 Kb long.

In the invention, genes for luciferase and for luciferin, as well as other proteins, promoters, targeting sequences, selection sequences and control sequences may be inserted in place of the T-DNA. This insertion may occur via a single transformation or by way of two or more serial transformations, depending upon the quantity of DNA ultimately being inserted. Transfection of target plant cells by *Agrobacterium* will then result in plant cells in which the desired polynucleotide sequences have been incorporated into the plant's native genome. By exposing the plant cell to appropriate amounts of hormones and nutrients, a fully mature plant may be developed from the single transfected cell. The *A. tumefaciens* plasmid only transfects dicotyledon cells, thus limiting its use. However, *A. rhizogenes* has been found to successfully transfect monocotyledon cells utilizing a similar plasmid.

Metal microparticles may be coated with a desired recombinant DNA, and this recombinant DNA may be the same polynucleotide described above. The DNA-coated microparticles are then accelerated using gunpowder, helium gas or other methods known to those skilled in the art, to a velocity such that they may penetrate the plant cell. Micro-injection is another method of transforming plants. A microscopic needle is utilized to penetrate, and inject DNA directly into, the nucleus of the target plant cell.

Another transformation method suitable for all plant cell types is electroporation. Electroporation involves shocking the plant cells with a powerful electric pulse, momentarily disrupting the cell membrane and causing pores to form therein. Recombinant polynucleotides in the surrounding solution then enter the plant cell through these pores.

Yet another method of transforming plant cells is to expose them to polyethylene glycol (PEG). Exposure of plant cell protoplasts to PEG makes them momentarily permeable. Like electroporation, this allows the DNA in a surrounding solution to simply seep into the cell.

Another method of transforming plant cells includes the use of silicone fibers. The selection of the most suitable method of transformation will depend on a variety of factors, such as the type of plant cell being transformed, the type of luciferase and luciferin genes being utilized, the size of the recombinant DNA molecule to be inserted, the available facilities, and the relative expense of each method.

Bacterial artificial chromosomes (BACs) may be used to transform plant cells with recombinant polynucleotide fragments up to 350 Kb long. Furthermore, the Ti plasmid from

*Agrobacterium rhizogenes* has been found to successfully transfect monocotyledon cells. Binary vectors, like pBIN20, are plasmids that contain the Ti plasmid and bordering sequences, allowing them to also transfect plant cells.

In plant cells transformed and grown into a mature plant, the bioluminescent mechanism encoded by the recombinant DNA will be expressed subject to any associated promoter or promoters and will cause the plant to bioluminesce.

In one illustrative embodiment of the invention disclosed herein, three separate plasmids may be constructed, replicated in *E. coli*, and independently transfected or incorporated into a native *Agrobacterium* genome using electroporation, and the resulting *Agrobacterium* plasmids can be subsequently utilized to transfect plant cells. The vector and plasmid design and construction may vary, particularly in relation to the amount or quantity of recombinant DNA to be transfected.

Plasmid pLuxAB/pUCD2715

For this construct, the luxAB fusion gene (SEQ ID NO: 10) and plasmid pUCD2715 are utilized as described by Clarence I. Kado, "Live Time Quantification of Bacterial Interactions in Various Environments", Microbial Genome Methods, 192-194 (Kenneth W. Adolph, Ed.)(CRC Press, 1996), and Okumura et al., "Enhanced Stable Expression of a *Vibrio* Luciferase Under the Control of the Ω-translational Enhancer in Transgenic Plants", World Journal of Microbiology and Biotechnology 8:638-644 (November 1992), which publications are incorporated herein by reference.

With respect to FIG. 1, plasmid pLuxAB/pUCD2715 100 includes the NOS promoter 102, which regulates the expression of the hph gene 104, which encodes resistance to the antibiotic hygromycin for selection of the plasmid in plant cells. 35S promoter 106 regulates the expression of the luxAB fusion gene 110. Situated between them is the Ω-3 translational enhancer 108. Origin of replication region 114 contains sequences recognized by DNA polymerase for replication of plasmid pLuxAB/pUCD2715 100 in an *E. coli* culture, while origin of replication region 112 contains sequences for replication in *Agrobacterium*. Plasmid pLuxAB/pUCD2715 100 further includes selection sequence 116, which encodes resistance to the antibiotic kanamycin for selection of the plasmid in *Agrobacterium*.

Optionally, a targeting sequence may be cloned into plasmid pLuxAB/pUCD2715 100. This targeting sequence preferably codes for an additional peptide sequence that is added to the N-terminus of the luciferase enzyme encoded by the luxAB fusion gene 110. This targeting sequence causes the intracellular machinery to direct the luciferase enzyme to a specific organelle or region of the cell. The targeting sequence may direct proteins to a variety of organelles including, but not being limited to, the Golgi apparatus, mitochondria, chloroplasts, lysosomes, peroxisomes, or the nucleosome. In the absence of a targeting sequence, the luciferase/luciferin bioluminescence reaction will go forward in the cytosol. However, targeting the enzyme and its substrate to a specific organelle may be advantageous for a number of reasons. Various organelles may have optimal internal pH or higher concentrations of oxygen, ATP, or other co-factors to facilitate the luciferase/luciferin reaction. Furthermore, directing all of the luciferase and luciferin to a selected organelle will result in a higher relative concentration of the enzymes and accelerate the reaction. This has the result of shortening the length of time it takes to consume the luciferin, but it also increases the brightness of the bioluminescent plant.

Plasmid pLuxC[ires]D

An internal ribosome entry site (IRES) facilitates the expression of multiple genes in eukaryotic cells using a single promoter. A known synthetic IRES, synthesized by Midland Scientific, Inc. of Omaha, Nebr. and described by Ivanov et al., "A tobamovirus genome that contains an internal ribosome entry site functional in vitro", Virology 232(1):32-43 (May 1997) has the following sequence (SEQ ID NO: 1):

```
GGATCCGTCGACGAATTCGTCGATTCGGTTGCAGCATTTAAAGCGGTTGA

CAACTTTAAAAGAAGGAAAAAGAAGGTTGAAGAAAAGGGTGTAGTAAGTA

AGTATAAGTACAGACCGGAGAAGTACGCCGGTCCTGATTCGTTTAATTTG/

AAAGAAGAAAATGTCCCGGGCTGCAG
```

This IRES is cloned into pGEM®-3Z (PROMEGA CORP., MADISON, Wis.) between the PstI and BamH1 restriction sites, thus forming an intermediate construct "pIRES".

The luxC gene is PCR® amplified from the p607 plasmid (which contains the entire lux operon; see Kado, supra and Okumura et al., supra; used with permission) using the following primers:

```
C Forward
                                          (SEQ ID NO: 2)
    GGTCTAGACAGTTTAAAAAAGCAGTCT C Reverse
                                          (SEQ ID NO: 3)
    GGGGATCCCTTGATGATGTGATCAATCG
```

The amplification product is then cut with XbaI and with BamHI, and cloned into the 35S-CaMV cassette (JOHN INNES CENTRE, NORWICH, UK) between the XbaI and BamHI restriction sites, thus forming an intermediate construct "p35S-C-CaMV".

The luxD gene is amplified from p607 using the following primers:

```
D Forward
                                          (SEQ ID NO: 4)
    GGCCCGGGTGTCCCATAGTTAAAGGAAA D Reverse
                                          (SEQ ID NO: 5)
    GGGAATTCATTCCTTTTTGGTGATTCTG
```

This amplification product is then cloned into the pBlue-TOPO™ (INVITROGEN CORP., CARLSBAD, Calif.) vector using a topoisomerase cloning protocol, thus forming an intermediate construct "pBlue-D".

The cloned luxD gene is excised from "pBlue-D" using HindIII and cut into "pIRES" using HindIII. The resulting plasmid, a construct entitled "pIRES-D", can be verified by cutting with EcoRI and analyzing restriction fragments.

The IRES-luxD sequence is cut out of "pIRES-D" using EcoRI and cloned into "p35S-C-CaMV" using EcoRI. The resulting construct is "p35S-C-IRES-D-CaMV" and can be verified by cutting with SacI and analyzing restriction fragments.

The "p35S-C-IRES-D-CaMV" sequence is excised from the cassette using EcoRV and moved into plasmid pGreenI 0029 (JOHN INNES CENTRE, NORWICH, UK) using EcoRV, thus completing the pLuxC[ires]D plasmid. The pLuxC[ires]D plasmid is grown in *E. coli* cultures using methods and materials that are well known in the art.

With respect to FIG. 2, plasmid pLuxC[ires]D 200 is comprised of a cloning region 202 flanked by a left border 206 and a right border 208. Left border 206 and right border 208 each correspond to a BglII restriction site 204 for the insertion or excision of cloning region 202. 35S promoter 214 regulates expression of the luxC gene 216, the internal ribosome entry site 218, and the luxD gene 220. NOS promoter 222 regulates the downstream expression of selection sequence 224. Selection sequence 224 encodes resistance to the antibiotic geneticin for selection of the plasmid in plant cells. The nptI (neomycin phosphotransferase) gene 226 encodes resistance to the antibiotic kanamycin for selection of the plasmid in *Agrobacterium*. Origin of replication region 212 contains sequences recognized by DNA polymerase for replication of plasmid pLuxC[ires]D 200 in an *E. coli* culture, while origin of replication region 210 contains sequences for replication in *Agrobacterium*.

Plasmid pLuxE[ires]Frp

The luxE gene is amplified from p607 using the following primers:

```
E Forward
                                           (SEQ ID NO: 6)
GGCTCGAGTTAGGTATTACTGGAGAGGG E Reverse
                                           (SEQ ID NO: 7)
GGGTCGACTGAAACTCTACCATCAACAA
```

The amplification product is then cut with XhoI and with SalI.

The frp gene from *Vibrio harveyi* is amplified using the following primers:

```
frp Forward
                                           (SEQ ID NO: 8)
GGCTGCAGGCTCCCAATAAATGCCGTTA frp Reverse
                                           (SEQ ID NO: 9)
GGACTAGTTGGCAGCGTATGGTCAAAAT
```

The amplification product is then cut with PstI and SpeI.

Both of these products are then cloned into intermediate vector pCR-TOPO™ (INVITROGEN CORP., CARLSBAD, Calif.). The luxE gene is excised from the intermediate vector using XhoI and EcoRI, and cloned into a NOS cassette (JOHN INNES CENTRE, NORWICH, UK) using XhoI and EcoRI, thus forming intermediate construct "pNOS-E".

The frp gene is excised from the intermediate vector using PstI and HindIII and cloned into "pIRES" (see plasmid pLuxC[ires]D above), thus forming intermediate construct "pIRES-Frp", which is in turn cut with EcoRI and cloned into "pNOS-E" using EcoRI. This results in a construct having the sequence "pNOS-E-IRES-Frp", which is excised from its cassette using EcoRV and cloned into plasmid pGreenII 0179 (JOHN INNES CENTRE, NORWICH, UK), to complete the pLuxE[ires]Frp plasmid. The pLuxE[ires] Frp plasmid is grown in *E. coli* cultures.

With respect to FIG. 3, plasmid pLuxE[ires]Frp 300 is comprised of a cloning region 302 flanked by a left border 306 and a right border 308. Left border 306 and right border 308 each correspond to a BglII restriction site 304, for the insertion or excision of cloning region 302. NOS promoter 314 regulates expression of the luxE gene 316, the internal ribosome entry site 318, and the frp gene 320. 35S promoter 322 regulates the downstream expression of selection sequence 324. Selection sequence 324 encodes resistance to the antibiotic hygromycin for selection of the plasmid in plant cells. The nptI (neomycin phosphotransferase) gene 326 encodes resistance to the antibiotic kanamycin, for selection of the plasmid in *Agrobacterium*. Origin of replication region 312 contains sequences recognized by DNA polymerase for replication of plasmid pLuxC[ires]D 200 in an *E. coli* culture, while origin of replication region 310 contains sequences for replication in *Agrobacterium*.

The actual restriction sites and restriction endonucleases to be utilized will be determined by the precise plasmid used. The choice of plasmid makes no difference. It is generally desirable to use different restriction sites on the 5' and 3' ends of insert recombinant DNA. This prevents plasmids from ligating to themselves without incorporating a recombinant DNA sequence.

Transfection of Plasmids into *Agrobacterium* and Transfection of Plant Cells

With respect to FIG. 4, plasmid pLuxC[ires]D 200 is transfected into a suitable *Agrobacterium* 400 along with helper plasmid pSoup 402 (JOHN INNES CENTRE, NORWICH, UK) via electroporation, using standard electroporation protocols well known in the art. Those skilled in the art will further appreciate that transfection will occur in a suitable buffer or other medium. The transfected *Agrobacterium* cells 404 are subjected to an appropriate amount of the antibiotic kanamycin 406, which selects for successful transfection. Negatively selected cells 408 are those which succumb to kanamycin 406. Successfully transfected *Agrobacterium* cells 410 remain in culture.

Successfully transfected *Agrobacterium* cells 410 are combined with a leaf fragment 412 having a torn portion 414 in a callus growth medium 416. The resulting callus 418 is subjected to an appropriate amount of the antibiotic geneticin 420, which selects for successfully transfected plant cells 422. Negatively selected plant cells 424 are those which succumb to geneticin 420.

Plasmid pLuxE[ires]frp 300 is transfected into a suitable *Agrobacterium* 400 along with helper plasmid pSoup 402 (JOHN INNES CENTRE, NORWICH, UK) via electroporation. Transfection will occur in a suitable buffer or other medium. The transfected *Agrobacterium* cells 426 are subjected to an appropriate amount of the antibiotic kanamycin 406, which selects for successful transfection. Negatively selected cells 428 are those which succumb to kanamycin 406. Successfully transfected *Agrobacterium* cells 430 remain in culture.

Successfully transfected *Agrobacterium* cells 430 are combined with successfully transfected plant cells 422 in a callus growth medium 416. The resulting callus 432 is subjected to an appropriate amount of the antibiotic hygromycin 434, which selects for successfully transfected plant cells 436. Negatively selected plant cells 438 are those which succumb to hygromycin 434.

Plasmid pLuxAB/pUCD2715 100 is transfected into a suitable *Agrobacterium* 400 along with helper plasmid pUCD2614 (see Kado, supra.) 440 via electroporation. Again, transfection will occur in a suitable buffer or other medium. The transfected *Agrobacterium* cells 442 are subjected to an appropriate amount of the antibiotic kanamycin 406, which selects for successful transfection. Negatively selected cells 444 are those which succumb to kanamycin 406. Successfully transfected *Agrobacterium* cells 446 remain in culture.

Successfully transfected *Agrobacterium* cells 446 are combined with successfully transfected plant cells 436 in a callus growth medium 416. Selection with hygromycin is optional, as successfully transfected mature plant may otherwise be selected on the basis of bioluminescence. The resulting callus 448 is grown into a mature transgenic plant 450.

The promoter regions selected may be any of a number of known promoter sequences; for example, certain known promoters down-regulate a downstream sequence when night falls, and therefore, the luciferase could stop being expressed around dusk. Down-regulating the foreign sequence allows the plant to conserve its energy, amino acids and ribosomes for natural functions. It is possible to utilize other promoters that are never turned off, i.e. constitutive promoters. It is also possible to utilize promoters that up-regulate at night and down-regulate during the day, as well as stress-linked promoters, which regulate expression under certain endogenous conditions, such as drought, infestation or disease. Because the bioluminescence of these plants can only be seen in the dark, it is preferred that such bioluminescence be regulated by the amount of light exposure. This is not necessary, however, and any appropriate promoter may be used. In flowering plants, it may be desirable to induce bioluminescence in the flowers themselves. Alternatively, it may be desirable in fruiting plants to induce bioluminescence only in the fruit. Plant promoters include CAB2, RuBisCO, NOS, and 35S.

LuxC 216, luxD 220 and luxE 316 encode polypeptides that help synthesize the aldehyde substrate required for the bioluminescene reaction. Other luciferins may require a different metabolic pathway, and therefore, an operon of one or more different genes in order to form intracellular luciferin.

In the illustrative embodiment, luxC 216 and luxD 220 are regulated by a 35S promoter 214. In another embodiment, these genes may be regulated by a circadian clock promoter that turns off in the nighttime. As such, bioluminescence in this particular example will only last a few hours after dusk. It may be desirable to utilize a promoter that turns on at dusk or that is not dependent upon the circadian clock, such as a stress-linked promoter.

The lux operon had originally been thought to be ineffective in plant cells. This is due, in part, to the lack of available flavin mononucleotide (FMN) that is not bound to flavoproteins and is both free within the cytosol and is present in its reduced state. $FMNH_2$ is a required co-factor for the lux bioluminescence reaction. A number of approaches may be taken to ensure that adequate $FMNH_2$ is present in the cytosol. In the invention disclosed herein, a flavin reductase gene frp 320 is incorporated into cloning region 302 of plasmid pLuxE[ires]Frp 300. Frp 320 may come from any known source, preferably from the bacterium *Vibrio harveyi*. Frp 320 and luxE 316 are introduced into *Agrobacterium* by way of a common plasmid pLuxE[ires]Frp 300, along with an internal ribosome entry site 318, but the vector and plasmid design and selection may vary.

Frp 320 and luxE 316 are downstream from promoter region 314. These genes may be regulated by the same or a different promoter than promoter region 214 (regulating luciferase). In the illustrative embodiment, luxE 316 and frp 320 are regulated by the NOS promoter. It is generally desirable that the FMN reductase protein be expressed in an amount sufficient to provide adequate amounts of $FMNH_2$ to facilitate bioluminescence, but over-expression of the FMN reductase protein may disrupt intracellular chemistry.

Another method of regulating the amount of intracellular $FMNH_2$ is to include within the transforming polynucleotide an operon encoding the proteins necessary for $FMNH_2$ catabolism. Appropriate promoter sequences may be used in order to provide an adequate amount of free $FMNH_2$ in the cytosol. This operon may or may not include an FMN reductase gene.

Yet another method of providing free $FMNH_2$ in the cytosol is to include in the transforming polynucleotide a control sequence that up-regulates the native $FMNH_2$ catabolic pathway within the plant cell. This up-regulating control sequence may itself be regulated by a promoter region that controls the degree of up-regulation of the native $FMNH_2$ catabolism operon.

This illustrative embodiment also includes an hph gene 104 (hygromycin resistance), a geneticin selection sequence 224 and a hygromycin selection sequence 324 for selection of the respective plasmids in plant cells, and a kanamycin selection sequence 116 and nptI gene 226/326 (hygromycin) for selection of the respective plasmids in *Agrobacterium*. Other ubiquitous antibiotic resistance selection sequences may be utilized, such as those that confer resistance to ampicillin or streptomycin. In addition, the hph gene 104 in pLuxAB/pUCD2715 100 is not necessary per se, because bioluminescence of the mature plant may itself serve as the selection marker for successful transfection of the luciferase gene. It is still possible to use antibiotic resistance or other selection markers, if desired.

It may be desirable to ensure that these transgenic bioluminescent plants are sterile. Persons who oppose the genetic modification of organisms may be more accepting of these plants if they are incapable of reproducing. When plants first sprout, a number of promoters are turned on or off. Several active promoters will eventually be turned off as the plant ages, while inactive promoters will be turned on over time. Recombinant polynucleotides having genes to be inserted into a plant's genome may include a sterility operon that is activated by an early development promoter region. This would cause the sterility operon to induce production of a toxin which would kill the seedling. This would prevent the plant from producing offspring. One such toxin is ribosomal inhibitory protein (RIP), which is well known in the art.

Not all luciferin catabolic pathways have been elucidated, however, there are a variety of methods to accomplish this. One such method is the utilization of a genomic library. For example, the entire genome of a particular species may be chopped into several shorter strands of DNA. Chromosomes are mixed with one or more restriction enzymes, resulting in the chromosomes being cut into many strands of DNA. The restriction enzymes are then deactivated by denaturation or other methods known in the art. The DNA strands are then inserted into plasmids, phagemids, cosmids or BACs.

Individual plant cells may be cultured in a petri dish, liquid media or other means known in the art. They are then transformed with the Ti plasmid or other methods as described above. This transformation is utilized to insert DNA coding for a luciferase protein. Using control sequences, such as kanamycin resistance disclosed above, is a common method for selectively growing transformed plant cells. Successfully transformed plant cells are capable of expressing luciferase. A CAB2 promoter, temperature-sensitive promoter, or other means may be used to regulate transcription and translation of the luciferase gene. Those plant cells having the luciferase gene inserted in them may then be transformed a second time, using the genomic library created by the method described above. The luciferase used in the initial transformation of the plant cells must come from the same species from which the DNA library is derived; however, luciferases from various species are generally incompatible with luciferins from other species.

A control sequence located within the plasmid, phagemid, cosmid or BAC used to make the genomic library is preferably different from the control sequence used in the initial transformation. For example, if the initial plasmid possesses kanamycin resistance, the second polynucleotide sequence to be transformed encodes resistance to another antibiotic, such as gentamycin. The twice-transformed plant cells may then be grown in media containing both kanamycin and gentamycin, such that it is selected only for plant cells that contain both plasmids. This results in selection for plants that have incorporated within them a luciferase gene and a portion of a genomic library. The operon coding for the luciferin catabolic pathway may be present in at least one of these twice-transformed plant cells. The plant cells are then grown under conditions that provide for expression of the luciferase gene and the genes of the genomic library. Any plant cells that catabolize luciferin will bioluminesce. These plant cells may then be grown into mature plants that bioluminesce.

Alternatively, plant cells that bioluminesce may be isolated so that the polynucleotide sequence responsible for luciferin catabolism may be identified. Once the luciferin catabolism operon has been isolated, it may be incorporated into the same plasmid, phagemid, cosmid or BAC as the original luciferase gene. This new transforming polynucleotide may then be used to transform plant cells, thereby providing bioluminescing plant cells by means of a single transformation. The cells may then be grown up into mature plants that bioluminesce.

In yet another illustrative embodiment of the invention disclosed herein, the bioluminescent plant may be further genetically engineered to express a phototransformative protein such as green fluorescent protein (GFP) from the jellyfish *Aequorea victoria*. To accomplish this, a suitable DNA sequence encoding the desired phototransformative protein is inserted into the plant's native genome. Phototransformative protein refers to any of a number of proteins that have the ability to capture and modify photons from a bioluminescent light source in such a way that light of a different wavelength is emitted. Other phototransformative proteins include those encoded by luxF and luxG from the bacterial lux operon, as well as known mutants, variants or analogs of GFP, including GFP isolated from the sea pansy, *Renilla reniformis*. For example, the phototransformative proteins may include green fluorescent proteins, such as EGFP, blue fluorescent proteins, such as EBFP, a cyan fluorescent protein, such as ECFP, a yellow fluorescent protein, such as EYFP, an orange fluorescent protein, such as DsRed or a red fluorescent protein, such as AsRed2.

GFP is a reporter that has been expressed in a wide variety of organisms. GFP absorbs blue light, such as that emitted from known bioluminescence pathways, and emits green light by means of fluorescence. Variants have slightly different excitation and emission peaks within the visible spectrum. The gene encoding GFP can be regulated with promoters, including stress-linked promoters, such that it is only expressed under certain conditions, including hydration, disease, infestation, temperature, ripeness, and adequacy of nutrients. For example, the stress-linked promoters can include a fungal-inducible promoter, such as the pRtlp1 promoter, a wound-inducible promoter, such as a wound-inducible gene of *Arabidopsis*, a general stress-inducible promoter, such as the Rd29A promoter, a phosphate-inducible promoter, such as the P1BS promoter or a nitrogen-inducible promoter, such as the nblA promoter or an ANR1-like MADS-box gene that regulates *Arabidopsis* root meristem behavior and mediates morphogenetic responses under nitrogen and phosphorus starvation.

The regulated emission of green light in the illustrative bioluminescent plant, either in lieu of or in addition to bioluminescence, serves as yet another means of communicating information about conditions either endogenous or exogenous to the plant. Moreover, green fluorescence may itself be utilized to screen or select those plants, which have been successfully transfected with GFP. Alternatively, successful transfection of GFP may be determined via an accompanying selection sequence conferring resistance to an antibiotic.

Whereas, the plants and methods have been described in relation to the drawings and claims, it should be understood that other and further modifications, apart from those shown or suggested herein, may be made within the scope of this invention.

What is claimed is:

1. A transgenic autoluminescent plant, comprising at least one plant cell having within its genome:
   a lux gene encoding a luciferase,
   a lux gene encoding a luciferin that is compatible with said luciferase,
   and at least one means for regulation of autoluminescent expression of said lux genes;
   wherein said means for regulation comprises at least one light-inducible promoter and/or inducible health-linked promoter operably linked to at least one of said lux genes.

2. The plant of claim 1 further comprising within said genome of said cell at least one gene encoding a phototransformative protein and at least one means for regulation of expression of said gene encoding said phototransformative protein.

3. The plant of claim 2 where said phototransformative protein is green fluorescent protein or a genetic mutant of green fluorescent protein.

4. The plant of claim 3 wherein said phototransformative protein is a green fluorescent protein, a blue fluorescent protein, a cyan fluorescent protein, a yellow fluorescent protein, an orange fluorescent protein or a red fluorescent protein.

5. The plant of claim 2 wherein said means for regulating expression of said gene encoding said phototransformative protein is a 5' promoter.

6. The plant of claim 1 wherein said inducible health-linked promoter regulates expression under a set of conditions selected from the group consisting of hydration, disease, infestation, temperature, ripeness, and adequacy of nutrients.

7. The plant of claim 6 wherein said inducible health-linked promoter is a fungal-inducible promoter, a wound-inducible promoter, a general stress-inducible promoter, a phosphate-inducible promoter or a nitrogen-inducible promoter.

8. The plant of claim 1 wherein said at least one light-inducible promoter is the RuBisCO 5' promoter or the CAB2 promoter.

9. A transgenic autoluminescent plant cell comprising within its genome:
   a lux gene encoding a luciferase,
   a lux gene encoding a luciferin that is compatible with said luciferase,
   and at least one means for regulation of autoluminescent expression of said lux genes;
   wherein said means for regulation comprises at least one light-inducible promoter and/or inducible health-linked promoter operably linked to at least one of said lux genes.

10. The plant cell of claim 9 further comprising a lux gene encoding a phototransformative protein.

11. The plant cell of claim 10 where said phototransformative protein is green fluorescent protein or a genetic mutant of green fluorescent protein.

12. The plant cell of claim 10 wherein said phototransformative protein is a green fluorescent protein, a blue fluorescent protein, a cyan fluorescent protein, a yellow fluorescent protein, an orange fluorescent protein or a red fluorescent protein.

13. The plant cell of claim 9 wherein said inducible health-linked promoter regulates expression under a set of conditions selected from the group consisting of hydration, disease, infestation, temperature, ripeness, and adequacy of nutrients.

14. The plant cell of claim 13 wherein said inducible health-linked promoter is a fungal-inducible promoter, a wound-inducible promoter, a general stress-inducible promoter, a phosphate-inducible promoter or a nitrogen-inducible promoter.

15. The plant cell of claim 9 wherein said at least one light-inducible promoter is the RuBisCO 5' promoter or the CAB2 promoter.

16. A transgenic autoluminescent plant seed comprising within its genome:
   a lux gene encoding a luciferase,
   a lux gene encoding a luciferin that is compatible with said luciferase,
   and at least one means for regulation of autoluminescent expression of said lux genes;
   wherein said means for regulation comprises at least one light-inducible promoter and/or inducible health-linked promoter operably linked to at least one of said lux genes.

17. The plant seed of claim 16 further comprising a lux gene encoding a phototransformative protein.

18. The plant seed of claim 17 where said phototransformative protein is green fluorescent protein or a genetic mutant of green fluorescent protein.

19. The plant seed of claim 17 wherein said phototransformative protein is a green fluorescent protein, a blue fluorescent protein, a cyan fluorescent protein, a yellow fluorescent protein, an orange fluorescent protein or a red fluorescent protein.

20. The plant seed of claim 16 wherein said inducible health-linked promoter regulates expression under a set of conditions selected from the group consisting of hydration, disease, infestation, temperature, ripeness, and adequacy of nutrients.

21. The plant seed of claim 20 wherein said inducible health-linked promoter is a fungal-inducible promoter, a wound-inducible promoter, a general stress-inducible promoter, a phosphate-inducible promoter or a nitrogen-inducible promoter.

22. The plant seed of claim 16 wherein said at least one light-inducible promoter is the RuBisCO 5' promoter or the CAB2 promoter.

* * * * *

SEQUENCE LISTING

```
<160> NUMBER OF SEQ ID NOS: 10

<210> SEQ ID NO 1
<211> LENGTH: 176
<212> TYPE: DNA
<213> ORGANISM: Artificial
<220> FEATURE:
<223> OTHER INFORMATION: Synthetic internal ribosome entry site

<400> SEQUENCE: 1
ggatccgtcg acgaattcgt cgattcggtt gcagcattta aagcggttga caactttaaa      60
agaaggaaaa agaaggttga agaaaagggt gtagtaagta agtataagta cagaccggag     120
aagtacgccg gtcctgattc gtttaatttg aaagaagaaa atgtcccggg ctgcag         176

<210> SEQ ID NO 2
<211> LENGTH: 27
<212> TYPE: DNA
```

```
<213> ORGANISM: Artificial
<220> FEATURE:
<223> OTHER INFORMATION: Synthetic primer sequence C forward

<400> SEQUENCE: 2
ggtctagaca gtttaaaaaa gcagtct                                            27

<210> SEQ ID NO 3
<211> LENGTH: 28
<212> TYPE: DNA
<213> ORGANISM: Artificial
<220> FEATURE:
<223> OTHER INFORMATION: Synthetic primer sequence C reverse

<400> SEQUENCE: 3
ggggatccct tgatgatgtg atcaatcg                                           28

<210> SEQ ID NO 4
<211> LENGTH: 28
<212> TYPE: DNA
<213> ORGANISM: Artificial
<220> FEATURE:
<223> OTHER INFORMATION: Synthetic prmier sequence D forward

<400> SEQUENCE: 4
ggcccgggtg tcccatagtt aaaggaaa                                           28

<210> SEQ ID NO 5
<211> LENGTH: 28
<212> TYPE: DNA
<213> ORGANISM: Artificial
<220> FEATURE:
<223> OTHER INFORMATION: Synthetic primer sequence D reverse

<400> SEQUENCE: 5
gggaattcat tcctttttgg tgattctg                                           28

<210> SEQ ID NO 6
<211> LENGTH: 28
<212> TYPE: DNA
<213> ORGANISM: Artificial
<220> FEATURE:
<223> OTHER INFORMATION: Synthetic primer sequence E forward

<400> SEQUENCE: 6
ggctcgagtt aggtattact ggagaggg                                           28

<210> SEQ ID NO 7
<211> LENGTH: 28
<212> TYPE: DNA
<213> ORGANISM: Artificial
<220> FEATURE:
<223> OTHER INFORMATION: Synthetic primer sequence E reverse

<400> SEQUENCE: 7
gggtcgactg aaactctacc atcaacaa                                           28

<210> SEQ ID NO 8
<211> LENGTH: 28
<212> TYPE: DNA
<213> ORGANISM: Artificial
<220> FEATURE:
<223> OTHER INFORMATION: Synthetic primer sequence frp forward

<400> SEQUENCE: 8
ggctgcaggc tcccaataaa tgccgtta                                           28
```

<210> SEQ ID NO 9
<211> LENGTH: 28
<212> TYPE: DNA
<213> ORGANISM: Artificial
<220> FEATURE:
<223> OTHER INFORMATION: Synthetic primer sequence frp reverse

<400> SEQUENCE: 9
ggactagttg gcagcgtatg gtcaaaat                                28

<210> SEQ ID NO 10
<211> LENGTH: 2505
<212> TYPE: DNA
<213> ORGANISM: Vibrio fischeri
<300> PUBLICATION INFORMATION:
<301> AUTHORS: K. Okumura, L. Chlumsky, T.O. Baldwin & C.I. Kado
<302> TITLE: Enhanced stable expression of a Vibrio luciferase under the
       control of the omega-translational enhancer in transgenic plants
<303> JOURNAL: World Journal of Microbiology and Biotechnology
<304> VOLUME: 8
<306> PAGES: 638-644
<307> DATE: 1992

<400> SEQUENCE: 10
ggatcccaag ctttattttt acaacaatta ccttacaatt actatttaca attacagtcg      60
actttatcga gcctgatttt gaacaactca ccatcgcgac tgtgaatgaa cgtcgcttga     120
aagcggaaat tgaaagccgt acgcaagaaa tggcttaggt cttatcgtaa taccaacaaa     180
taaggaaatg ttatgaaatt tggaaacttc cttctcactt atcagccacc tgagctatct     240
cagaccgaag tgatgaagcg attggttaat ctgggcaaag cgtctgaagg ttgtggcttc     300
gacaccgttt ggttgctaga gcaccacttc actgaatttg ggttgttagg aatcctttat     360
gttgctgccg cacacctatt agctgcgaca gaaacgctca acgttggcac tgcagctatc     420
gtattgccga ctgcccatcc ggttccacaa gcagaagacg taaacctact ggatcaaatg     480
tcaaaaggac gattccgttt tggtatttgt cgcggtttgt acgataaaga ttttcgtgtc     540
tttggtacag acatggataa cagccgagcc ttaatggact gttggtatga cttgatgaaa     600
gaaggcttca atgaaggcta tatcgcggcg ataacgaac atattaagtt cccgaaaatc      660
caactgaatc catcggctta cacacaaggt ggtgctcctg tttatgtcgt cgcggagtca     720
gcatcaacga cagaatgggc tgcagagcgt ggcctaccaa tgattctaag ctggatcatc     780
aacactcacg agaagaaagc gcagcttgat ctttacaacg aagtcgcgac tgaacatggc     840
tacgatgtga ctaagattga ccactgtttg tcttacatca cctccgtcga tcatgactca     900
aatagagcca agatatttg ccgcaacttc ttgggccatt ggtacgactc atacgtgaat      960
gccaccaaga tttttgacga ctctgaccaa acaaaaggtt acgacttcaa taaggtcaa     1020 tggcgtgatt ttgtgttgaa aggccacaaa gacaccaatc gccgaattga ttacagctac     1080
gaaatcaacc cagtagggac gcctgaagag tgtatcgcga ttatccagca agatattgat     1140
gcgacgggta ttgacaatat tgttgtggt tttgaagcaa acggttctga agaagaaatt      1200
atcgcatcta tgaagctatt ccagtctgat gtgatgccat atctcaaaga aaaacagatc     1260
ttaagtattg ttttaaacag gctcgagcat tcgacaaaag tgttagtgga gccacgcgcg     1320
ccagaatcca gaacttcgaa atttggatta ttcttcctca attttatgaa ttcaaagcgt     1380
tcttctgatc aagtcatcga agaaatgtta gataccgcac attacgtaga tcagttgaag     1440
tttgacacgt tggctgttta cgaaaaccat ttctcgaaca atggtgtggt tggtgccccca    1500

```
ctaacagtgg ctggtttttt acttggtatg acaaagaacg ccaaagtggc ttcgttgaat  1560
cacgtcatta ccacgcatca tccagtacgt gtggcggaag aagcgtgtct acttgaccaa  1620
atgagtgaag gccgttttgc ctttggcttt agtgattgtg aaaagagtgc acatatgcgc  1680
ttctttaatc gaccaacgga ttctcagttt cagttgttca gtgagtgtca caagatcatc  1740
aatgatgcat tcactactgg gtactgccat ccaaacaatg attttttatag ttttcctaaa  1800 atctccgtta acccacacgc gttcactgaa ggcggtcctg cgcaatttgt gaatgcgacg  1860
agcaaagaag tggttgaatg ggcggctaag ttagggcttc cactcgtgtt tagatgggac  1920
gactcaaacg ctcaaagaaa agaatacgcc cgtttgtacc acgaagttgc tcaggcacat  1980
ggtgtcgatg ttagtcaggt tcgacacaag ctgacgctgc tggtcaacca aaatgtagat  2040
ggtgaagcag caagggcaga agctcgcgtg tatttggaag agtttgtccg tgaatcttac  2100
tcaaataccg actttgagca aaaaatggga gagctgttgt cagaaaatgc catcggtact  2160
tatgaagaaa gtactcaggc agcgcgagtt gcgattgagt gttgtggtgc cgcggaccta  2220
ttgatgtctt ttgagtcgat ggaagataaa gcgcagcaaa gagcggttat cgatgtggta  2280
aacgccaaca tcgtcaaata ccactcgtaa cgtttaactg atgctgaagg ggcagcgatg  2340 cccttatat caccattctt ttcgccgata gcgctaacta atagaggcat ttatatggac  2400
gtactttcag cggttaagca ggaaaacatc gcagcgagca cagaaatcga tgacttgatt  2460
ttcatgggaa ctcctcagca atggtcattg caggaacaaa aacag             2505
```